United States Patent
Geiselhart et al.

(10) Patent No.: US 7,900,630 B2
(45) Date of Patent: Mar. 8, 2011

(54) GAS DELIVERY MASK WITH FLEXIBLE BELLOWS

(75) Inventors: Edward M. Geiselhart, Chicago, IL (US); Chris Houghton, Chicago, IL (US); Erik Holverson, Naperville, IL (US); Brian Woodard, Chicago, IL (US); Steve Trebotich, Newark, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1206 days.

(21) Appl. No.: 11/155,195

(22) Filed: Jun. 17, 2005

(65) Prior Publication Data
US 2006/0283456 A1 Dec. 21, 2006

(51) Int. Cl.
*A62B 18/08* (2006.01)
(52) U.S. Cl. .......... 128/206.24; 128/206.27; 128/207.11; 128/205.25
(58) Field of Classification Search ............. 128/206.21, 128/206.24, 206.26–206.28, 206.18, 206.12, 128/207.11, 207.13, 205.25
See application file for complete search history.

(56) References Cited

U.S. PATENT DOCUMENTS

| | | | |
|---|---|---|---|
| 1,081,745 A | 12/1913 | Johnston et al. | |
| 1,532,195 A | 4/1925 | Morrison | |
| 1,911,938 A | 5/1933 | Bard | |
| 2,130,155 A | 9/1938 | Malcom | |
| 2,428,451 A | 10/1947 | Emerson | |
| 3,824,999 A | 7/1974 | King | 128/185 |
| 4,069,516 A | 1/1978 | Watkins, Jr. | 72/201 |
| 4,275,908 A | 6/1981 | Elkins et al. | 285/55 |
| 4,373,520 A | 2/1983 | Arbique | 128/201.19 |
| 4,498,472 A | 2/1985 | Tanaka | 128/205.17 |
| 4,539,983 A | 9/1985 | Angell | 128/201.19 |
| 4,739,755 A | 4/1988 | White et al. | 128/206.12 |
| 4,799,263 A | 1/1989 | Banziger et al. | 381/94 |
| 4,843,686 A | 7/1989 | Bartholomew | 24/19 |
| 4,875,718 A | 10/1989 | Marken | 285/175 |
| 4,886,056 A | 12/1989 | Simpson | 128/201.25 |
| 4,915,106 A | 4/1990 | Aulgur et al. | 128/207.11 |
| 4,938,209 A | 7/1990 | Fry | 128/200.21 |
| 4,958,633 A | 9/1990 | Angell | 128/201.19 |
| 4,960,121 A | 10/1990 | Nelson et al. | 128/206.24 |
| 4,989,596 A | 2/1991 | Macris et al. | 128/201.28 |
| 5,036,846 A | 8/1991 | Aulgur et al. | 128/207.11 |

(Continued)

FOREIGN PATENT DOCUMENTS

EP 1025875 2/2000

(Continued)

OTHER PUBLICATIONS

International Preliminary Report on Patentability PCT/US2006/023234, 7 pages, Jan. 3, 2008.

(Continued)

*Primary Examiner* — Steven O Douglas

(57) ABSTRACT

A gas delivery mask apparatus is provided. The mask apparatus may include a mask body, a face mask, and a bellows. The mask body may include a tube configured to extend upwardly adjacent a subject's forehead. The face mask may be configured to deliver gas to the subject and may include a flexible cushion portion configured to interface with the subject's face and a substantially rigid base portion configured to support the cushion portion. The bellows may be configured to couple the tube with the substantially rigid base portion of the face mask. The bellows may be flexible to allow movement of the face mask relative to the tube.

24 Claims, 8 Drawing Sheets

U.S. PATENT DOCUMENTS

| | | | | |
|---|---|---|---|---|
| 5,038,776 | A | 8/1991 | Harrison et al. | 128/207.11 |
| 5,054,482 | A | 10/1991 | Bales | 128/207.14 |
| 5,058,244 | A | 10/1991 | Fernandez | 24/170 |
| D321,418 | S | 11/1991 | Dolida et al. | D29/7 |
| 5,069,205 | A | 12/1991 | Urso | 128/201.24 |
| 5,074,297 | A | 12/1991 | Venegas | 124/204.18 |
| 5,181,280 | A | 1/1993 | Zachry, Jr. | 2/452 |
| 5,181,507 | A | 1/1993 | Michel et al. | 128/201.25 |
| 5,199,424 | A | 4/1993 | Sullivan et al. | 128/204.18 |
| 5,269,296 | A | 12/1993 | Landis | 128/207.18 |
| 5,353,789 | A | 10/1994 | Schlobohm | 128/206.24 |
| 5,429,126 | A | 7/1995 | Bracken | 128/207.11 |
| 5,429,683 | A | 7/1995 | Le Mitouard | 128/206.24 |
| 5,441,046 | A | 8/1995 | Starr et al. | 128/207.11 |
| 5,463,693 | A | 10/1995 | Birli et al. | 381/75 |
| 5,503,147 | A | 4/1996 | Bertheau | 128/207.11 |
| 5,517,986 | A | 5/1996 | Starr et al. | 128/206.24 |
| 5,537,994 | A | 7/1996 | Thornton | 128/204.18 |
| 5,567,752 | A | 10/1996 | Stein et al. | 524/188 |
| 5,623,923 | A | 4/1997 | Bertheau et al. | 128/207.11 |
| 5,628,305 | A | 5/1997 | Melker | 128/202.29 |
| 5,662,101 | A | 9/1997 | Ogden et al. | 128/205.25 |
| 5,697,363 | A | 12/1997 | Hart | 128/201.24 |
| 5,724,965 | A | 3/1998 | Handke et al. | 128/207.13 |
| 5,921,239 | A | 7/1999 | McCall et al. | 128/205.25 |
| 5,941,245 | A | 8/1999 | Hannah et al. | 128/207.11 |
| 5,975,490 | A | 11/1999 | Essman | 251/149.4 |
| 6,039,045 | A | 3/2000 | Bertheau et al. | 128/207.11 |
| 6,041,781 | A | 3/2000 | Aglan | 128/205.17 |
| 6,044,844 | A | 4/2000 | Kwok et al. | 128/207.11 |
| 6,112,746 | A * | 9/2000 | Kwok et al. | 128/207.13 |
| 6,119,694 | A | 9/2000 | Correa et al. | 128/207.13 |
| 6,123,071 | A | 9/2000 | Berthon-Jones et al. | 128/204.18 |
| 6,155,253 | A | 12/2000 | Gamberini | 128/201.18 |
| 6,164,829 | A | 12/2000 | Wenzel et al. | 384/203 |
| 6,182,298 | B1 | 2/2001 | Dampney | 2/422 |
| 6,192,886 | B1 | 2/2001 | Rudolph | 128/207.13 |
| 6,263,874 | B1 | 7/2001 | LeDez et al. | |
| 6,279,172 | B1 | 8/2001 | Epperson et al. | 2/410 |
| 6,338,342 | B1 | 1/2002 | Fecteau et al. | 128/207.11 |
| 6,347,631 | B1 | 2/2002 | Hansen et al. | 128/207.11 |
| 6,357,441 | B1 | 3/2002 | Kwok et al. | 128/207.13 |
| 6,374,824 | B1 | 4/2002 | Thornton | 128/201.26 |
| 6,374,826 | B1 | 4/2002 | Gunaratnam et al. | 128/206.27 |
| 6,382,206 | B1 | 5/2002 | Palazzotto et al. | 128/201.19 |
| 6,386,198 | B1 | 5/2002 | Rugless | 128/206.21 |
| 6,435,181 | B1 | 8/2002 | Jones, Jr. et al. | 128/204.18 |
| 6,439,230 | B1 | 8/2002 | Gunaratnam et al. | 128/206.21 |
| 6,463,931 | B1 | 10/2002 | Kwok et al. | 128/207.11 |
| 6,467,483 | B1 | 10/2002 | Kopacko et al. | 128/207.12 |
| 6,470,886 | B1 | 10/2002 | Jestrabek-Hart | 128/207.11 |
| 6,494,207 | B1 | 12/2002 | Kwok | 128/207.11 |
| 6,497,232 | B2 | 12/2002 | Fecteau et al. | 128/207.11 |
| 6,505,623 | B1 | 1/2003 | Hansen | 128/207.11 |
| 6,516,802 | B2 | 2/2003 | Hansen et al. | 128/207.11 |
| 6,530,373 | B1 | 3/2003 | Patron et al. | 128/205.25 |
| 6,532,961 | B1 | 3/2003 | Kwok et al. | 128/206.21 |
| 6,536,435 | B1 | 3/2003 | Fecteau et al. | 128/207.11 |
| 6,539,941 | B2 | 4/2003 | Haubeil | 128/205.13 |
| 6,543,445 | B1 | 4/2003 | Hopper | 128/200.4 |
| 6,571,797 | B1 | 6/2003 | Magidson et al. | 128/205.27 |
| 6,581,594 | B1 | 6/2003 | Drew et al. | 128/204.18 |
| 6,581,602 | B2 | 6/2003 | Kwok et al. | 128/207.13 |
| 6,591,837 | B1 | 7/2003 | Byram | 128/206.24 |
| 6,595,214 | B1 * | 7/2003 | Hecker et al. | 128/207.13 |
| 6,615,830 | B1 | 9/2003 | Serowski et al. | 128/202.27 |
| 6,615,834 | B2 | 9/2003 | Gradon et al. | 128/207.11 |
| 6,619,288 | B2 | 9/2003 | Demers et al. | 128/205.25 |
| 6,619,570 | B1 | 9/2003 | Ericksen et al. | 239/532 |
| 6,626,178 | B2 | 9/2003 | Morgan et al. | 128/206.26 |
| 6,629,532 | B2 | 10/2003 | Campbell, Sr. | 128/207.11 |
| 6,668,830 | B1 | 12/2003 | Hansen et al. | 128/206.21 |
| D486,226 | S | 2/2004 | Guney et al. | D24/110.1 |
| D486,907 | S | 2/2004 | Guney et al. | D24/110.1 |
| 6,691,708 | B2 | 2/2004 | Kwok et al. | 128/207.11 |
| 6,694,973 | B1 | 2/2004 | Dunhao et al. | 128/203.12 |
| 6,701,926 | B2 | 3/2004 | Olsen et al. | 128/207.11 |
| 6,701,927 | B2 | 3/2004 | Kwok et al. | 128/207.13 |
| 6,729,333 | B2 | 5/2004 | Barnett et al. | 128/207.13 |
| 6,732,733 | B1 | 5/2004 | Brostrom et al. | 128/206.27 |
| 6,745,770 | B2 | 6/2004 | McAuliffe et al. | 128/205.24 |
| 6,745,772 | B1 | 6/2004 | McLeod | 128/206.21 |
| 6,772,760 | B2 | 8/2004 | Frater et al. | 128/206.24 |
| 6,776,161 | B2 | 8/2004 | Horn | 128/207.11 |
| 6,789,541 | B2 | 9/2004 | Olsen et al. | 128/207.11 |
| 6,792,947 | B1 | 9/2004 | Bowden | 128/205.17 |
| 6,805,117 | B1 | 10/2004 | Ho et al. | 128/201.22 |
| 6,820,615 | B1 | 11/2004 | Feng | 128/201.27 |
| 6,851,425 | B2 | 2/2005 | Jaffre et al. | 128/204.18 |
| 6,851,428 | B2 | 2/2005 | Dennis | 128/205.25 |
| 6,854,465 | B2 | 2/2005 | Bordewick et al. | 128/207.11 |
| 6,883,519 | B2 | 4/2005 | Schmidtke et al. | 128/207.11 |
| 6,886,564 | B2 | 5/2005 | Sullivan et al. | 128/206.24 |
| 6,895,964 | B2 | 5/2005 | McAuliffe et al. | 128/205.24 |
| 6,907,882 | B2 | 6/2005 | Ging et al. | 128/207.11 |
| 6,926,004 | B2 | 8/2005 | Schumacher | 128/206.27 |
| 6,926,007 | B2 | 8/2005 | Frank | 128/846 |
| 6,951,218 | B2 | 10/2005 | Gradon et al. | 128/205.25 |
| 6,959,710 | B2 | 11/2005 | Barnett et al. | 128/207.13 |
| 6,981,503 | B1 | 1/2006 | Shapiro | 128/845 |
| 7,017,576 | B2 | 3/2006 | Olsen et al. | 128/205.25 |
| 7,017,579 | B2 | 3/2006 | Palmer | 128/207.17 |
| 7,036,508 | B2 | 5/2006 | Kwok | 128/207.11 |
| 7,047,971 | B2 | 5/2006 | Ho et al. | 128/207.11 |
| 7,047,972 | B2 | 5/2006 | Ging et al. | 128/207.11 |
| 7,059,326 | B2 * | 6/2006 | Heidmann et al. | 128/207.11 |
| 7,066,179 | B2 | 6/2006 | Eaton et al. | 128/206.27 |
| 7,089,941 | B2 | 8/2006 | Bordewick et al. | 128/207.11 |
| 7,096,867 | B2 | 8/2006 | Smith et al. | 128/207.11 |
| 7,188,620 | B2 | 3/2007 | Amarasinghe | 128/201.22 |
| 7,201,169 | B2 | 4/2007 | Wilkie et al. | 128/207.18 |
| 7,207,335 | B2 | 4/2007 | Kwok et al. | 128/207.12 |
| 7,231,921 | B2 | 6/2007 | Palmer | 128/207.17 |
| 7,318,439 | B2 | 1/2008 | Raje et al. | 128/206.24 |
| 7,320,323 | B2 | 1/2008 | Lang et al. | 128/206.24 |
| 7,357,136 | B2 | 4/2008 | Ho et al. | 128/207.11 |
| 2002/0096176 | A1 | 7/2002 | Gunaratnam et al. | 128/207.11 |
| 2002/0148473 | A1 | 10/2002 | Kwok et al. | 128/207.11 |
| 2002/0157668 | A1 | 10/2002 | Bardel | 128/201.22 |
| 2002/0189616 | A1 | 12/2002 | Wolf | 128/205.25 |
| 2003/0000001 | A1 | 1/2003 | McDonald et al. | 2/6.3 |
| 2003/0005935 | A1 | 1/2003 | Kwok et al. | 128/206.21 |
| 2003/0019496 | A1 | 1/2003 | Kopacko et al. | 128/206.24 |
| 2003/0051732 | A1 | 3/2003 | Smith et al. | 128/206.27 |
| 2003/0075180 | A1 | 4/2003 | Raje et al. | 128/206.24 |
| 2003/0075182 | A1 | 4/2003 | Heidmann et al. | 128/207.11 |
| 2003/0084903 | A1 | 5/2003 | Fecteau et al. | 128/206.27 |
| 2003/0087033 | A1 | 5/2003 | Ramsay | 427/282 |
| 2003/0127096 | A1 | 7/2003 | McAuliffe et al. | 128/204.18 |
| 2003/0127101 | A1 | 7/2003 | Dennis | 128/206.21 |
| 2003/0164170 | A1 | 9/2003 | Drew et al. | 128/204.18 |
| 2003/0196655 | A1 | 10/2003 | Ging et al. | 128/201.22 |
| 2003/0217746 | A1 | 11/2003 | Gradon et al. | 128/201.26 |
| 2003/0221691 | A1 | 12/2003 | Biener et al. | 128/206.24 |
| 2004/0025882 | A1 | 2/2004 | Madaus et al. | 128/206.27 |
| 2004/0034519 | A1 | 2/2004 | Huitouze et al. | 704/1 |
| 2004/0065328 | A1 | 4/2004 | Amarasinghe et al. | 128/206.27 |
| 2004/0073989 | A1 | 4/2004 | Horn | 2/42 |
| 2004/0083534 | A1 | 5/2004 | Ruiz et al. | 2/171.2 |
| 2004/0107964 | A1 | 6/2004 | Shaw | 128/203.22 |
| 2004/0112377 | A1 | 6/2004 | Amarasinghe et al. | 128/201.22 |
| 2004/0112384 | A1 | 6/2004 | Lithgow et al. | 128/206.21 |
| 2004/0118406 | A1 | 6/2004 | Lithgow et al. | 128/206.24 |
| 2004/0182396 | A1 | 9/2004 | Dennis | 128/205.25 |
| 2004/0182398 | A1 | 9/2004 | Sprinkle et al. | 128/207.13 |
| 2004/0194783 | A1 | 10/2004 | McAuliffe et al. | 128/205.24 |
| 2004/0216746 | A1 | 11/2004 | Jones, Jr. et al. | 128/206.21 |
| 2004/0221850 | A1 | 11/2004 | Ging et al. | 128/206.27 |
| 2004/0226566 | A1 | 11/2004 | Gunaratnam et al. | 128/207.18 |
| 2004/0255949 | A1 | 12/2004 | Lang et al. | 128/206.24 |
| 2005/0051171 | A1 | 3/2005 | Booth | 128/206.18 |
| 2005/0072428 | A1 | 4/2005 | Ho et al. | 128/205.25 |
| 2005/0076913 | A1 | 4/2005 | Ho et al. | 128/206.27 |
| 2005/0081858 | A1 | 4/2005 | Raje et al. | 128/206.21 |
| 2005/0155604 | A1 | 7/2005 | Ging et al. | 128/206.21 |
| 2005/0205096 | A1 | 9/2005 | Matula, Jr. et al. | 128/207.11 |
| 2005/0205694 | A1 | 9/2005 | Li | 239/587.4 |

| | | | |
|---|---|---|---|
| 2005/0279367 A1 | 12/2005 | Klemperer | 128/861 |
| 2005/0284481 A1 | 12/2005 | Meyer et al. | 128/207.11 |
| 2006/0000476 A1 | 1/2006 | Salem | 128/206.21 |
| 2006/0027236 A1 | 2/2006 | Barnett et al. | 128/206.24 |
| 2006/0032504 A1 | 2/2006 | Burton et al. | 128/207.11 |
| 2006/0042629 A1 | 3/2006 | Geist | 128/206.24 |
| 2006/0060200 A1 | 3/2006 | Ho et al. | 128/206.24 |
| 2006/0076019 A1 | 4/2006 | Ho | 128/206.24 |
| 2006/0090760 A1 | 5/2006 | Gradon et al. | 128/206.27 |
| 2006/0112961 A1 | 6/2006 | Aly | 128/206.11 |
| 2006/0118117 A1 | 6/2006 | Berthon-Jones et al. | 128/206.21 |
| 2006/0118119 A1 | 6/2006 | Berthon-Jones et al. | 128/207.11 |
| 2006/0162729 A1 | 7/2006 | Ging et al. | 128/206.27 |
| 2006/0174892 A1 | 8/2006 | Leksutin et al. | 128/207.11 |
| 2006/0191539 A1 | 8/2006 | Ho et al. | 128/207.11 |
| 2006/0207600 A1 | 9/2006 | Burrow et al. | 128/207.11 |
| 2006/0213521 A1 | 9/2006 | Radney | 128/207.11 |
| 2006/0225740 A1 | 10/2006 | Eaton et al. | 128/206.24 |
| 2006/0231102 A1 | 10/2006 | Bordewick et al. | 128/207.11 |
| 2006/0231103 A1 | 10/2006 | Matula, Jr. et al. | 128/207.13 |
| 2006/0272646 A1 | 12/2006 | Ho et al. | 128/207.11 |
| 2006/0283452 A1 | 12/2006 | Woodard et al. | 128/206.25 |
| 2006/0283456 A1 | 12/2006 | Geiselhart et al. | 128/206.24 |
| 2006/0283457 A1 | 12/2006 | Woodard et al. | 128/206.24 |
| 2006/0283458 A1 | 12/2006 | Woodard et al. | 128/206.24 |
| 2006/0283460 A1 | 12/2006 | Brown et al. | 128/206.24 |
| 2006/0283461 A1 | 12/2006 | Lubke et al. | 128/207.11 |
| 2007/0017525 A1 | 1/2007 | Madaus et al. | 128/207.11 |
| 2007/0028919 A1 | 2/2007 | Ho | 128/204.18 |
| 2007/0044797 A1 | 3/2007 | Ho | 128/204.18 |
| 2007/0062539 A1 | 3/2007 | Gunaratnam et al. | 128/207.18 |
| 2007/0107723 A1 | 5/2007 | Berg | 128/200.26 |

FOREIGN PATENT DOCUMENTS

| | | |
|---|---|---|
| EP | 0988869 | 3/2000 |
| EP | 1057494 B1 | 6/2000 |
| EP | 1057494 A2 | 12/2000 |
| EP | 1327458 | 1/2003 |
| EP | 1356843 | 4/2003 |
| EP | 1334742 | 8/2003 |
| EP | 1334742 A2 | 8/2003 |
| FR | 1083873 | 1/1955 |
| JP | 2000102615 | 4/2000 |
| JP | 2003175106 | 6/2003 |
| WO | 00/50122 | 8/2000 |
| WO | 0100266 A2 | 1/2001 |
| WO | 02/15968 | 8/2001 |
| WO | 02/096342 | 12/2002 |
| WO | 02096342 A2 | 12/2002 |
| WO | 03/008044 | 1/2003 |
| WO | 03/033077 | 4/2003 |
| WO | 03028613 A2 | 4/2003 |
| WO | 2004/018014 | 3/2004 |
| WO | 2004/021960 | 3/2004 |
| WO | 2004/022146 | 3/2004 |
| WO | 2004/022147 | 3/2004 |
| WO | 2004/041342 | 5/2004 |
| WO | 2004/078228 | 9/2004 |
| WO | 2004096332 A1 | 11/2004 |
| WO | 2005021075 A1 | 3/2005 |
| WO | 2005/034829 | 4/2005 |
| WO | 2005032634 A1 | 4/2005 |
| WO | 2005039680 A1 | 5/2005 |

OTHER PUBLICATIONS

International Search Report with Written Opinion, PCT/US2006/023083, 12 pages, Oct. 4, 2006.
International Search Report with Written Opinion, PCT/US2006/023109, 13 pages, Oct. 6, 2006.
International Search Report with Written Opinion, PCT/US2006/023110, 4 pages, Oct. 9, 2006.
International Search Report with Written Opinion, PCT/US2006/023234, 11 pages, Oct. 13, 2006.
International Search Report with Written Opinion, PCT/US2006/023100, 10 pages, Oct. 17, 2006.
International Search Report with Written Opinion, PCT/US2006/023090, 19 pages, Oct. 30, 2006.
International Preliminary Report on Patentability PCT/US2006/023100, 6 pages, Jan. 3, 2008.
International Preliminary Report on Patentability PCT/US2006/023083, 7 pages, Jan. 3, 2008.
International Preliminary Report on Patentability PCT/US2006/023090, 10 pages, Jan. 3, 2008.
International PCT Search Report with Written Opinion, PCT/US2006/023090, 19 pages, Mailed Oct. 30, 2006.
International PCT Search Report, PCT/US2006/023083, 3 pages, Mailed Oct. 4, 2006.
International PCT Search Report, PCT/US2006/023234, 3 pages, Mailed Oct. 13, 2006.
International PCT Search Report, PCT/US2006/023100, 2 pages, Mailed Oct. 17, 2006.

* cited by examiner

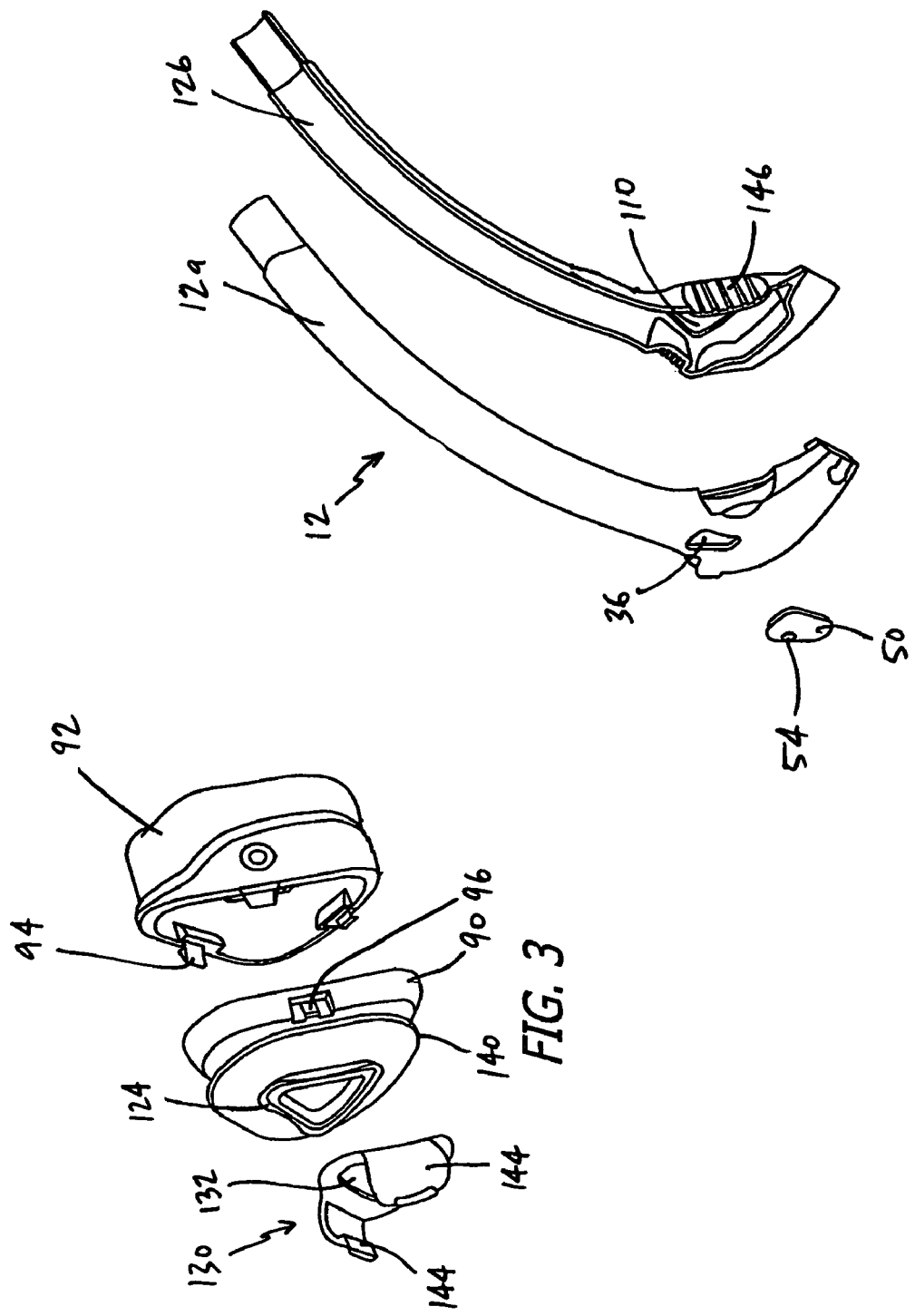

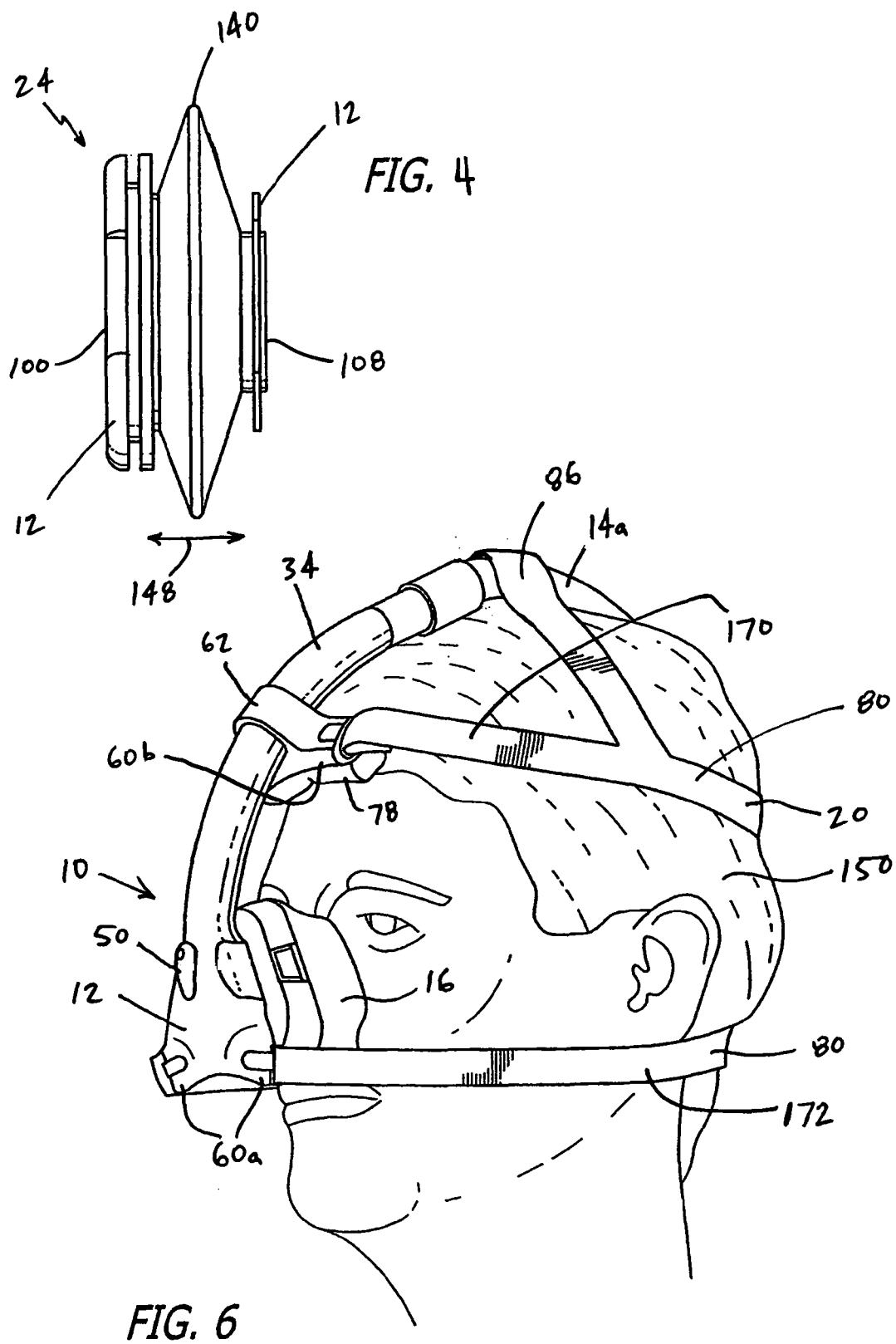

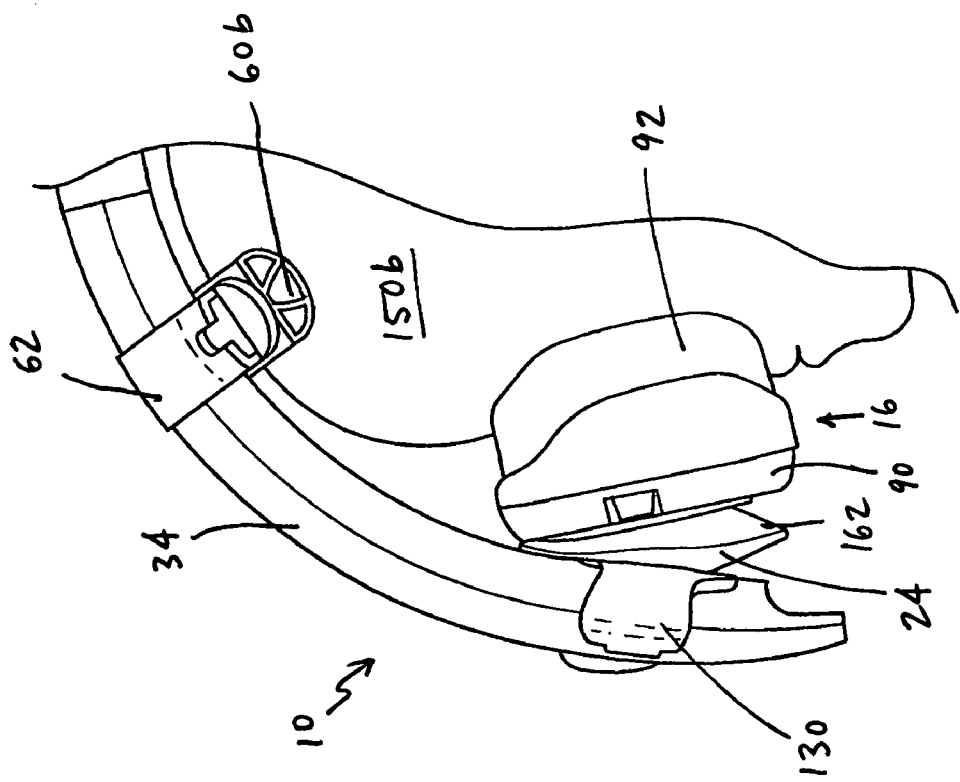
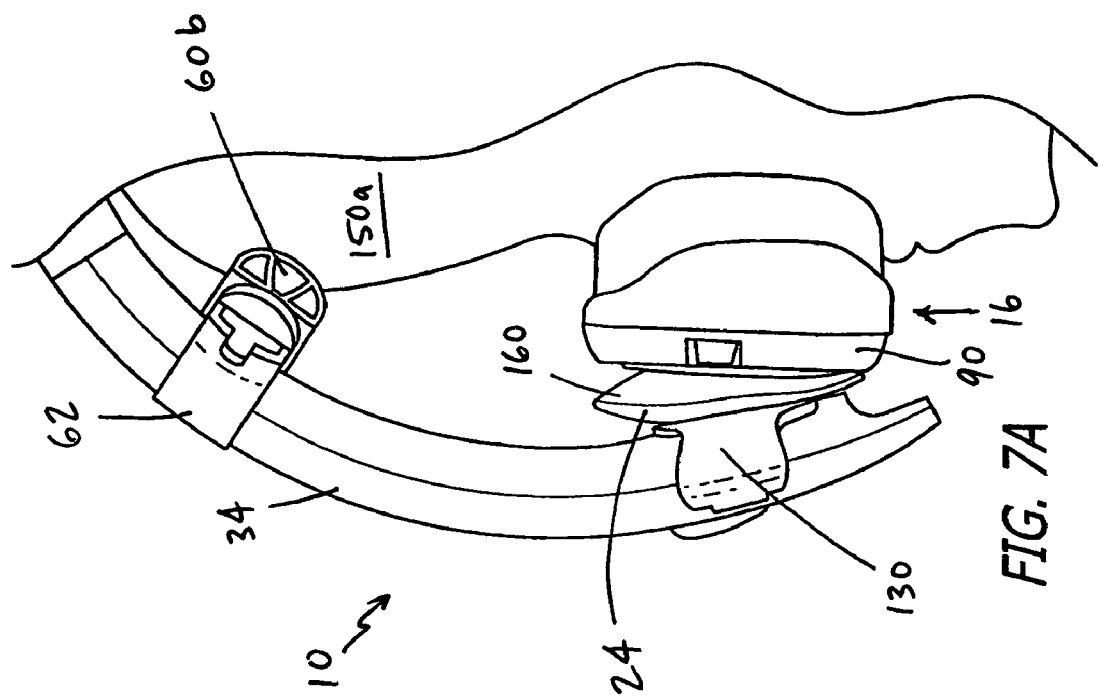
FIG. 7B
FIG. 7A

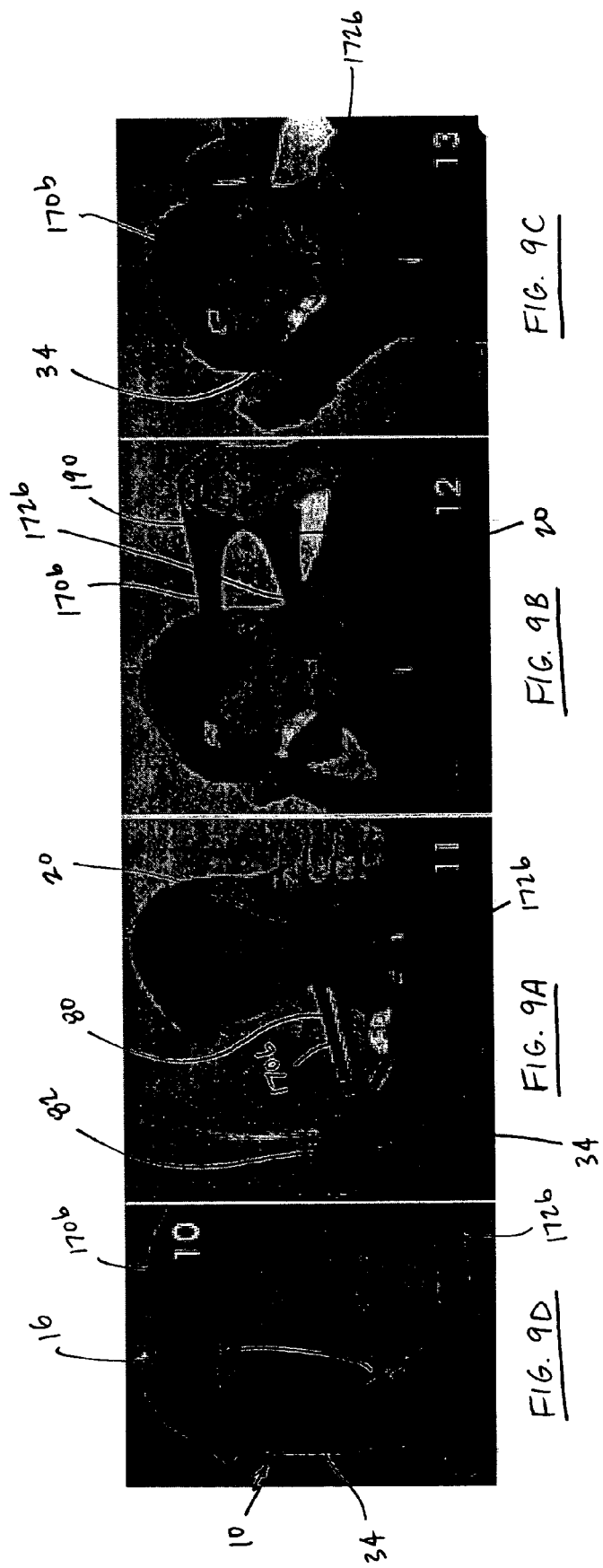

US 7,900,630 B2

GAS DELIVERY MASK WITH FLEXIBLE BELLOWS

TECHNICAL FIELD

The present disclosure is related to a gas delivery mask, e.g., a continuous positive airway pressure (CPAP) mask, having a flexible bellows for adjustability of the mask.

BACKGROUND

In recent years, continuous positive airway pressure (CPAP) therapy has become a common prescription for individuals suffering from sleep apnea and/or other breathing ailments. Such therapy may involve placement of a nose or face mask on the subject during sleeping, while positive pressure air is continuously delivered to the subject through the mask. In some cases, such CPAP treatment may materially lessen the incidents and/or severity of sleep apnea, thereby allowing the subject to sleep or rest with less disturbances.

A common problem encountered with prior CPAP nose mask assemblies is the tendency to leak positive pressure air at one or more locations, such as between connections of mask assembly components and/or between the mask assembly and the subject's face, e.g., where the cheek regions and nose intersect. Leaks between the mask and the subject's face are particularly common due to the wide ranges of shapes and sizes of the heads and faces of different subjects. Leaks within a mask assembly or between the mask assembly and the subject's face may be undesirable for various reasons. For example, leaks may reduce the positive pressure of the air being delivered to the subject. As another example, leaks between the mask and the subject's face may tends to dry the subject's eyes, creating uncomfortable wearing and operating conditions. As another example, leaks may produce noises, which may be undesirable to the subject and/or the subject's bed partner. One typical way to reduce leaks is to provide a tighter compressive fit of the mask against the nose and face of the wearer. However, too tight of a fit may cause discomfort to the subject.

SUMMARY

In accordance with the present disclosure, a gas delivery mask, e.g., a continuous positive airway pressure (CPAP) mask, having a flexible bellows for adjustability of the mask is provided.

In accordance with one embodiment of the present disclosure, a gas delivery mask apparatus is provided. The mask apparatus may include a mask body, a face mask, and a bellows. The mask body may include a tube configured to extend upwardly adjacent a subject's forehead. The face mask may be configured to deliver gas to the subject and may include a flexible cushion portion configured to interface with the subject's face and a substantially rigid base portion configured to support the cushion portion. The bellows may be configured to couple the tube with the substantially rigid base portion of the face mask. The bellows may be flexible to allow movement of the face mask relative to the tube.

In accordance with another embodiment of the present disclosure, a gas delivery mask apparatus is provided. The mask apparatus may include a mask body, a face mask, a head strap, and a strap support. The mask body may include a curved tube configured to extend upwardly adjacent a subject's forehead. The face mask may be configured to interface with the subject's face to deliver gas to the subject and may be flexibly coupled to the mask body such that the face mask may move relative to the mask body. The head strap may be configured to secure the mask body adjacent the subject's head. The strap support may be configured to support the head strap and may be movably coupled to the curved tube such that the strap support may be selectively positioned along a length of the curved tube.

In accordance with yet another embodiment of the present disclosure, a gas delivery mask apparatus is provided. The mask apparatus may include a body means, a face interface means, and a bellows means. The body means may include a gas conduit means configured to extend upwardly adjacent a subject's forehead. The face interface means may be configured to deliver gas to the subject and may include a flexible cushioning means configured to interface with the subject's face and a substantially rigid base means configured to support the flexible cushioning means. The bellows means may be configured to couple the gas conduit means with the substantially rigid base means of the face interface means. The bellows means may be flexible to allow movement of the face interface means relative to the gas conduit means.

BRIEF DESCRIPTION OF THE DRAWINGS

Some embodiments of the disclosure may be understood by referring, in part, to the following description and the accompanying drawings, in which like reference numbers refer to the same or like parts, and wherein:

FIG. 3 illustrates a partially exploded view of a face mask, a bellows, and a bellows clip, according to one embodiment of the disclosure;

FIG. 4 illustrates a side view of a bellows, according to one embodiment of the disclosure;

FIG. 5 illustrates an exploded view of a mask body and an exhaust port, according to one embodiment of the disclosure;

FIG. 6 illustrates an example embodiment of a mask apparatus secured to a subject's head, according to one embodiment of the disclosure;

FIG. 7A is a side view illustrating an adjustable mask apparatus secured to a relatively large head, such as an adult's head, according to one embodiment of the disclosure;

FIG. 7B is a side view illustrating an adjustable mask apparatus secured to a relatively small head, such as a child or infant's head, according to one embodiment of the disclosure;

FIGS. 9A-9D illustrate an example method of securing a mask assembly to a subject's head by securing strap portions of a head strap to each other, according to one embodiment of the disclosure.

DETAILED DESCRIPTION

Figure 1:
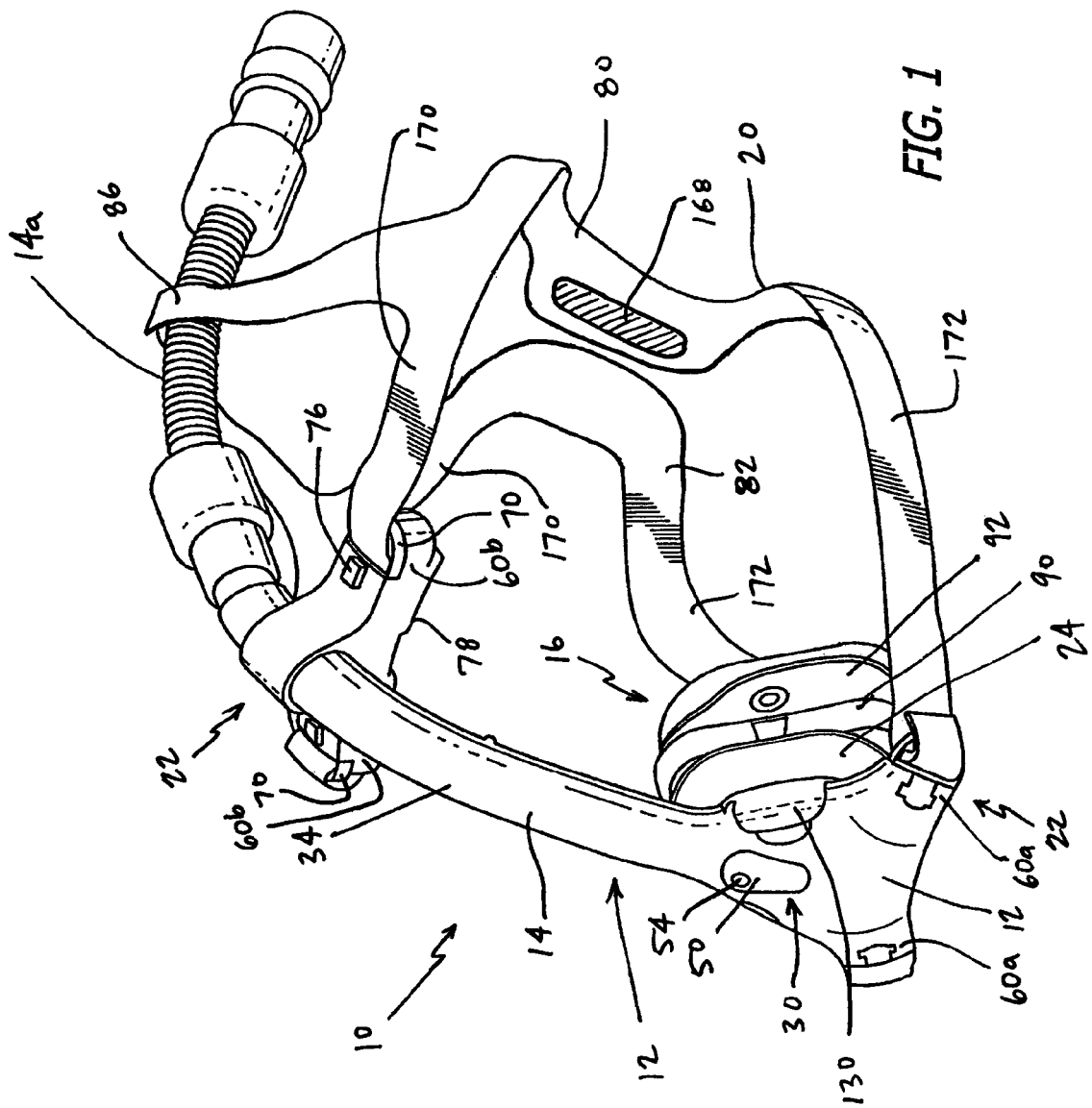
FIG. 1 is a three-dimensional assembled view of gas delivery mask apparatus, according to certain embodiments of the disclosure.
Figure 2:
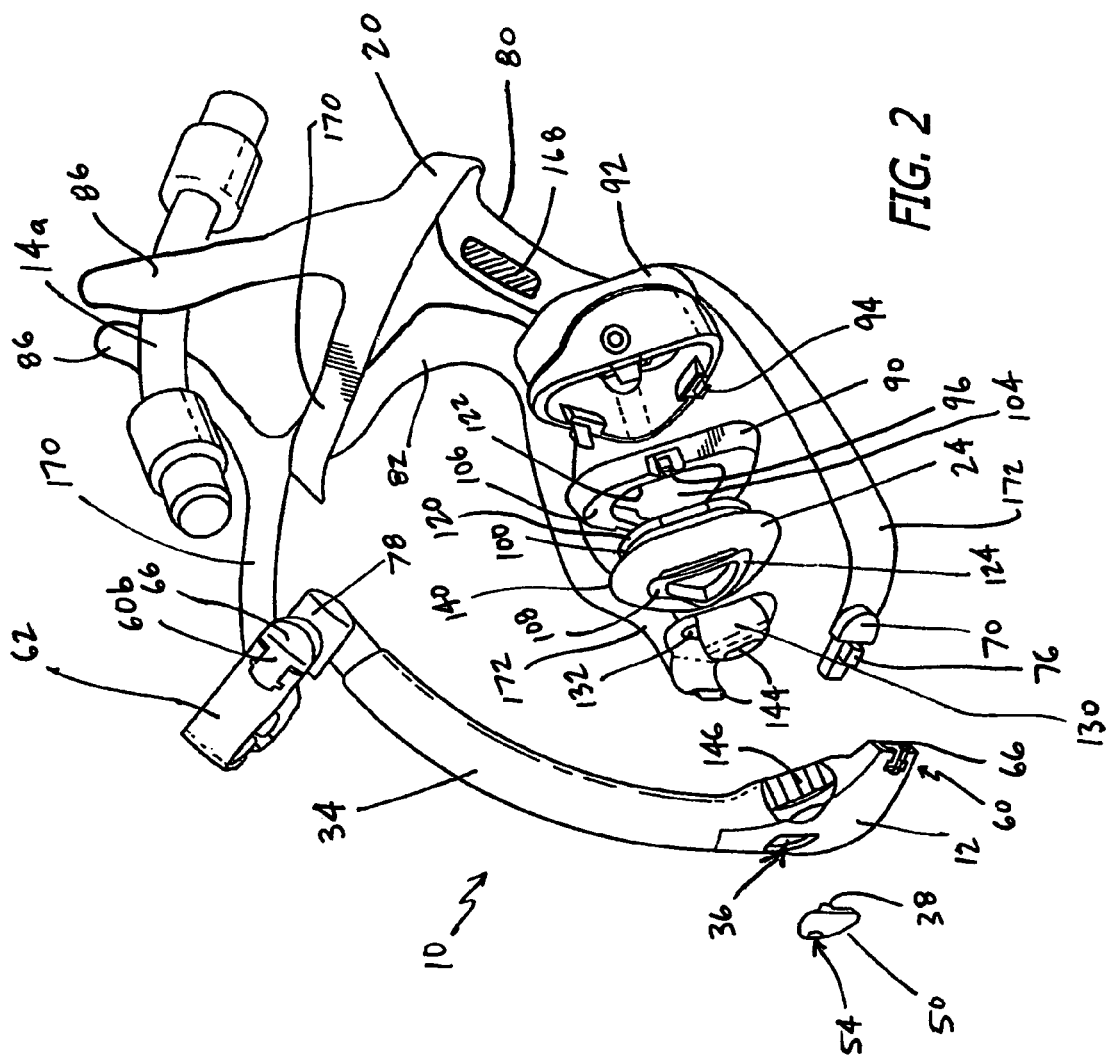
FIG. 2 is a three-dimensional unassembled, or exploded, view of a gas delivery mask apparatus, according to certain embodiments of the disclosure.

Selected embodiments of the disclosure may be understood by reference, in part, to FIGS. 1-9D, wherein like number refer to same and like parts FIGS. 1 and 2 illustrate a gas delivery mask apparatus 10 according to certain embodiments of the disclosure. More particularly, FIG. 1 is a three-dimensional assembled view of gas delivery mask apparatus 10, and FIG. 2 is a three-dimensional unassembled, or exploded, view of gas delivery mask apparatus 10.

Gas delivery mask apparatus 10 may be generally configured to assist a subject with breathing by delivering gas to the subject and/or removing gas from a subject, for example. As used herein, the term "gas" may refer to any one or more gases and/or vaporized substances suitable to be delivered to and/or from a subject via one or more breathing orifices (e.g., the nose and/or mouth), such as air, nitrogen, oxygen, any other component of air, $CO_2$, vaporized water, vaporized medicines, and/or any combination of two or more of the above, for example.

In a particular application, mask apparatus 10 may be used to provide constant positive air pressure (CPAP) to a subject, such as to treat an apnea or other breathing condition. In certain embodiments, such as described herein, mask apparatus 10 may be adjustably secured to the subject's head.

In various embodiments, gas delivery mask apparatus 10 may include one, some or all of the following features:

(a) a mask body 12, configured to, e.g., support one or more gas delivery conduits 14 and/or a face mask 16;

(b) a cushioned face mask 16 that may interface with the subject's face, such as around the nose and/or mouth openings;

(c) one or more gas delivery conduits 14 to, e.g., deliver one or more gases to and/or from the subject via face mask 16;

(d) one or more head straps 20 configured to, e.g., secure mask apparatus 10 on the subject's head;

(e) a head strap adjustment system 22 to, e.g., adjust the positioning of mask strap 20 and/or mask body 12 relative to the subject's head;

(f) a bellows 24 flexibly coupling face mask 16 to the mask body 12 such that face mask 16 may move (e.g., rotate and/or translate) relative to mask body 12; and (g) a gas exhaust system 30 to, e.g., remove exhaled gas away from the subject.

It should be understood that in various embodiments, gas delivery mask apparatus 10 may include any combination of one, some or all of these listed features (a)-(g) and/or any one or more additional features. For example, in certain embodiments (such as the embodiment shown and discussed below with reference to FIG. 2, for example), gas delivery mask apparatus 10 may include all of the listed features (a)-(g). In another example embodiment, mask apparatus 10 may include each listed feature except feature (e). In another example embodiment, mask apparatus 10 may include each listed feature except features (f).

In some embodiments, mask apparatus 10 may be a component of a breathing facilitation system that may facilitate or otherwise affect a subject's breathing, e.g., a CPAP system. Such a breathing facilitation system may include a mask apparatus 10, a gas (e.g., air) source, and/or one or more gas delivery conduits coupling mask apparatus 10 to the gas source such that gas may be delivered from the gas source to the subject via mask apparatus 10. The one or more gas delivery conduits may include all or portions of gas delivery pathway 28 and/or one or more addition gas delivery conduits or components for communicating gas between the gas source and mask apparatus 10. The gas source may be any device or devices configured to generate and/or supply gas (e.g., pressurized air) to a subject via mask apparatus 10. In some embodiments, the gas source may be configured to generate and/or supply pressurized gas (e.g., pressurized air) to a subject via mask apparatus 10. For example, the pressurized gas source may include a stand-alone unit capable of generating pressurized air (e.g., by pressurizing atmospheric air), a wall outlet through which pressurized air may be supplied (e.g., in a hospital or clinic), a tank of compressed air, or any other suitable source of pressurized air. In other embodiments, the gas source may be configured to generate and/or supply generally non-pressurized gas (e.g., atmospheric air), e.g., where breathing facilitation system is configured to provide clean or fresh air to a subject.

In addition, in some embodiments, the breathing facilitation system may include one or more devices to treat or condition the gas being delivered to the subject. For example, the breathing facilitation system may include one or more filters configured to filter the gas being delivered to the subject, a humidifier configured to humidify the gas being delivered to the subject, a heater or cooler configured to adjust and/or control the temperature of gas being delivered to the subject, and/or a medicine delivery device configured to deliver a medication (e.g., in vapor form) into the gas being delivered to the subject. In addition, in some embodiments, the breathing facilitation system may include a controller configured to control various parameters of the operation of the breathing facilitation system (e.g., to control various parameters of the operation of the pressurized gas source), and/or one or more sensors or other devices configured to provide feedback to the controller for regulating the operation of the breathing facilitation system. It should be understood that the breathing facilitation system may include any combination of one, some or all of the components discussed above and/or any one or more additional suitable components.

Mask body 12 may be generally configured to be mounted adjacent a subject's head and to, e.g., support various other components of mask apparatus 10, including, e.g., one or more gas delivery conduits 14, face mask 16, head strap 20 and/or head strap adjustment system 22. In some embodiments, such as shown in FIG. 1, mask body 12 may include a tube portion 34 that may serve as a gas delivery conduits 14 deliver one or more gases to and/or from a subject via face mask 16. Tube portion 34 may be coupled in any suitable manner to one or more other gas delivery conduits 14, such as gas delivery conduit 14a, for example. Thus, in the embodiment shown in FIG. 1, tube portion 34 may provide a conduit for communicating gas between conduit 14a and face mask 16.

Tube portion 34 may have any suitable shape and/or configuration. For example, in certain embodiments, tube portion 34 is a generally curved elongated tube configured to extend upwardly along, or adjacent to, a subject's forehead. A portion of tube portion 34 may curve over the subject's forehead and extend generally toward the back of the subject's head, such as shown and discussed below with reference to FIG. 6, for example. Tube portion 34 and/or mask body 12 may be formed from any suitable material. In some embodiments, tube portion 34 and/or mask body 12 may be formed from a suitable plastic or polymer. In a particular embodiment, tube portion 34 and/or mask body 12 may be formed from a relatively rigid polycarbonate.

Tube portion 34 may also include an opening 36 that may be configured to receive or be integrated with a gas exhaust system 30 allowing gas to escape from tube portion 34 to the surrounding environment. Gas exhaust system 30 may include any system for removing exhaled gas away from the subject. For example, gas exhaust system 30 may include a gas exhaust member 50 configured to allow gas exhaled by the subject (e.g., $CO_2$) to escape from mask apparatus 10 into the surrounding environment. In the embodiment shown in FIGS. 1 and 2, exhaust member 50 may include a lip 38 that may be secured within opening 36 in tube portion 34. In other embodiments, exhaust member 50 may be otherwise coupled to, or integrated with, tube portion 34 and/or mask body 12 in any suitable manner.

Exhaust member 50 may include an opening 54 extending though the member such that a gas passageway may be provided that extends from the open portion of face mask 16 that may interface with the subject's face, through face mask 16, bellows 24, tube portion 34, and out through opening 54 in exhaust member 50. Opening 54 in exhaust member 50 may be appropriately sized to allow a desired amount of gas flow through exhaust member 50 and/or to reduce or minimize noise created by gas flowing through exhaust member 50. In addition, in some embodiments, opening 54 may be oriented at an angle relative to general direction of gas flow between tube portion 34 and face mask 16, which may provide various benefits. For example, the angle of opening 54 may reduce and/or minimize the flow of exhaust gas incident upon another person, such as the subject's bed partner.

One or more strap supports 60 may be coupled to and/or integrated with mask body 12. In the embodiment shown in FIGS. 1 and 2, a first pair of strap supports 60a may be integrated with mask body 12, and a second pair of strap supports 60b may be formed in a strap guide 62 coupled to tube portion 34 of mask body 12. Strap supports 60 may be generally configured to support or couple one or more head straps 20 to mask body 12 in any suitable manner. In this embodiment, each strap support 60 may include a receptacle 66 for receiving and/or securing a strap clip 70. Receptacles 66 may comprise any one or more suitable notches, slots, clips or other elements for receiving and/or securing a strap clip 70.

Each strap clip 70 may be integrated with, coupled to, or secured to, a head strap 20 in any suitable manner. In the embodiment shown in FIGS. 1 and 2, each strap clip 70 may include an opening or eyelet through which a portion of a head strap 20 is routed or threaded in order to secure that strap clip 20 to the head strap 20. For example, an elongated portion of a head strap 20 may be routed through an opening or eyelet formed in a strap clip 70, folded or routed back, and attached to itself or another portion of the head strap 20 in any suitable manner, such as by hook and loop fasteners (e.g., Velcro™), adhesive, or stitching, for example.

In some embodiments, strap clips 70 are removably secured in receptacles 66 such that strap clips 70 may be repeatedly removed from and/or re-secured in receptacles 66. For example, in one embodiment, each strap clip 70 may include a button or tab 76 that may be pressed in order to release that the strap clip 70 from a receptacle 66 in which the strap clip 70 is secured.

In some embodiments, one or more strap supports 60 may be movable or adjustable with respect to tube portion 34 and/or mask body 12. For example, in the embodiment shown in FIG. 1, a pair of strap supports 60b integrated with a strap guide 62 may be movable or adjustable with respect to tube portion 34. Strap guide 62 may have an opening disposed around tube portion 34 such that strap guide 62 is slidably coupled to tube portion 34. Strap guide 62 may slide along at least a portion of the length of tube portion 34 to adjust the location and/or orientation of strap supports 60b relative to tube portion 34 and/or mask body 12. Thus, strap supports 60b may be adjusted such that mask assembly 10 may be adequately or desirably secured to a relatively wide range of head shapes and sizes, such as shown and described below with reference to FIGS. 7A and 7B, for example. In addition, because strap guide 62 may be configured to be secured against a subject's head, strap guide 62 may include a padded or cushion portion 78 configured to provide increased comfort to the subject.

Head strap(s) 20 may include any one or more components having any suitable shapes or configurations for securing mask apparatus 10 to a subject's head. For example, in the embodiment shown in FIGS. 1 and 2, an integrated head strap 20 includes a first strap portion 80 and a separate second strap portion 82. Strap portions 80 and 82 may be secured to supports 60 and removably attached to each other, e.g., using hook and loop fasteners (e.g., Velcro™) in order to secure mask assembly 10 to the subject's head. For example, one or both of strap portions 80 and 82 may include hook and loop fastener portions 168 configured to couple strap portions 80 and 82 to each other.

Strap portions 80 and/or 82 may include upper straps 170 generally configured to secure an upper portion of mask assembly 10 to the subject's head and lower straps 172 generally configured to secure a lower portion of mask assembly 10 (e.g., adjacent face mask 16) to the subject's head.

Strap portions 80 and/or 82 may include one or more support portions 86 configured to support and/or secure various components of mask assembly 10. For example, in the embodiment shown in FIGS. 1 and 2, each of strap portions 80 and 82 may include a support portion 86 configured to be coupled to each other to support and/or secure gas delivery conduit 14a. Support portions 86 may be coupled to each other and/or to other portions of head strap 20 in any suitable manner, e.g., using hook and loop fasteners (e.g., Velcro™). For example, a support portion 86 may include a hook and loop fastener portion 176 configured to couple support portion 86 to another support portion 86 and/or to another portion of head strap 20. In some embodiment, support portions 86 may help prevent one or more gas delivery conduits 14 from becoming crimped, tangled (e.g., around the subject's head or neck), or otherwise undesirably oriented due to movement of the subject.

Face mask 16 may be generally configured to be supported by tube portion 34 and/or mask body 12 and may interface with the subject's face, such as around the nose and/or mouth openings, to deliver gas to and/or remove gas from the subject. As discussed above, tube portion 34 may also comprise a gas delivery conduit 14 to, e.g., communicate gas to and/or from face mask 16. In this particular embodiment, gas may be delivered to the subject via a gas delivery pathway that may include a gas source (not shown), one or more gas delivery conduits 14 (e.g., tube portion 34 and/or gas delivery conduit 14a), bellows 24, and/or face mask 16.

In certain embodiments, face mask 16 may include a relatively rigid base portion 90 and/or a flexible, or pliable, cushion portion 92 coupled to base portion 90. Cushion portion 92 may be shaped and/or contoured to comfortably fit against a subject's face and/or to reduce or minimize the amount of gas that escapes from between cushion portion 92 and the subject's face. For example, cushion portion may have a 3-dimensional contour designed to fit against the contours of a subject's face.

In some embodiments, cushion portion 92 may be substantially flexible or pliable. For example, cushion portion 92 may be formed from a substantially flexible or pliable plastic, polymer, or silicone. In contrast, base portion 90 may be substantially rigid relative to cushion portion 92. For example, base portion 90 may be formed from a plastic or polymer more rigid than cushion portion 92.

Base portion 90 may be coupled to cushion portion 92 in any suitable manner, such as by clips, adhesive, or fasteners, for example. In the embodiment shown in FIG. 2, cushion portion 92 may include a number of tabs 94 proximate an outer perimeter of cushion portion 92 and extending toward base portion 90. Such tabs 94 may be received and locked into place in slots 96 formed proximate an outer perimeter of base portion 90. In some embodiments, base portion 90 may be removably coupled to cushion portion 92 in any suitable manner. For example, in this embodiment, once base portion 90 and cushion portion 92 are locked together (e.g., using tabs 94 and slots 96), base portion 90 may be separated from cushion portion 92 by squeezing cushion portion 92 proximate each tab/slot interface such that each tab 94 is released from its corresponding slot 96.

As discussed above, face mask 16 may be flexibly coupled to tube portion 34 by a bellows 24. In some embodiments, a first side 100 of bellows 24 may be coupled to and/or adjacent an opening 104 formed in a first side (or surface) 106 of base portion 90 of face mask 16, and a second side 108 of bellows 24 may be coupled to and/or adjacent an opening 110 formed in tube portion 34.

For example, in the embodiment shown in FIG. 2, a first lip 120 may be formed adjacent first side 100 of bellows 24. First lip 120 may generally define an opening in the first side 100 of bellows 24 having a cross-sectional shape $S_{120}$ and a cross-sectional area $A_{120}$. First lip 120 may be coupled to and/or adjacent opening 104 in first side (or surface) 106 of base portion 90 in any suitable manner. For example, first lip 120 may be removably secured to an inner edge 122 defined by opening 104. First side (or surface) 106 may have a cross-sectional shape $S_{106}$ and a cross-sectional area $A_{106}$. Similarly, opening 104 may have a cross-sectional shape $S_{104}$ and a cross-sectional area $A_{104}$. In some embodiments, cross-sectional shape $S_{104}$ and/or cross-sectional area $A_{104}$ of opening 104 may be substantially similar to cross-sectional shape $S_{120}$ and/or cross-sectional area $A_{120}$ of the opening defined by first lip 120. In addition, in some embodiments, cross-sectional area $A_{106}$ of first side (or surface) 106 of base portion 90 may be substantially larger than cross-sectional areas $A_{104}$ and/or $A_{120}$.

In addition, in the embodiment shown in FIG. 2, a second lip 124 may be formed adjacent second side 108 of bellows 24. Second lip 124 may generally define an opening in the second side 108 of bellows 24 having a cross-sectional shape $S_{108}$ and a cross-sectional area $A_{108}$. Second lip 124 may be coupled to and/or adjacent opening 110 formed in tube portion 34 in any suitable manner. For example, second lip 124 may be removably secured to or adjacent opening 110 by a bellows clip 130. Opening 110 may have a cross-sectional shape $S_{110}$ and a cross-sectional area $A_{110}$. Similarly, bellows clip 130 may have an opening 132 having a cross-sectional shape $S_{132}$ and a cross-sectional area $A_{132}$.

In some embodiments, cross-sectional shape $S_{108}$ and/or cross-sectional area $A_{108}$ of the opening defined by second lip 124 may be substantially similar to cross-sectional shape $S_{120}$ and/or cross-sectional area $A_{110}$ of opening 110 in tube portion 34. In addition, in some embodiments, cross-sectional shape $S_{132}$ and/or cross-sectional area $A_{132}$ of opening 132 in bellows clip 130 may be substantially similar to (a) cross-sectional shape $S_{108}$ and/or cross-sectional area $A_{108}$ of the opening defined by second lip 124 and/or (b) cross-sectional shape $S_{110}$ and/or cross-sectional area $A_{110}$ of opening 110 in tube portion 34.

In some embodiments, bellows 24 may include one or more pleats or folds 140. In the particular embodiment shown in FIG. 2, bellows 24 may include a single pleat 140 having a generally triangular perimeter and cross-section. Thus, pleat 140 may have a cross-sectional shape $S_{140}$ and/or cross-sectional area $A_{140}$. In some embodiments, cross-sectional shapes $S_{120}$, $S_{124}$, and $S_{140}$ of first lip 120, second lip 124, and pleat 140 of bellows 24 may have a substantially similar shape. In other embodiments, one or more of cross-sectional shapes $S_{120}$, $S_{124}$, and $S_{140}$ may have substantially different shapes. In particular embodiments, cross-sectional shapes $S_{120}$, $S_{124}$, and $S_{140}$ each have a generally triangular (e.g., a rounded triangular) shape.

In addition, in some embodiments, cross-sectional areas $A_{120}$, $A_{124}$, and $A_{140}$ of first lip 120, second lip 124, and pleat 140 of bellows 24 may be substantially similar. In other embodiments, one or more of cross-sectional areas $A_{120}$, $A_{124}$, and $A_{140}$ may be substantially different. For example, cross-sectional area $A_{140}$ of pleat 140 may be substantially larger than one or both cross-sectional areas $A_{120}$ and $A_{124}$ of first and second lips 120 and 124. In the particular embodiment shown in FIG. 2, cross-sectional areas $A_{120}$ of first lip 120 is larger than cross-sectional areas $A_{124}$ of second lip 124 and cross-sectional area $A_{140}$ of pleat 140 is substantially larger than each of cross-sectional areas $A_{120}$ and $A_{124}$.

In some embodiments, a first measurement is "substantially" different (e.g., larger or smaller) than a second measurement if the measurements differ by a factor of at least 1.2.

In some embodiments, one or more of cross-sectional shapes $S_{104}$, $S_{106}$, $S_{108}$, $S_{110}$, $S_{120}$, $S_{132}$, and $S_{140}$ may be substantially similar. In other embodiments, one or more of cross-sectional shapes $S_{104}$, $S_{106}$, $S_{108}$, $S_{110}$, $S_{120}$, $S_{132}$, and $S_{140}$ may be substantially different from each other. In a particular embodiment, each of cross-sectional shapes $S_{104}$, $S_{106}$, $S_{108}$, $S_{110}$, $S_{120}$, $S_{132}$, and $S_{140}$ may have a generally triangular (e.g., a rounded triangular) shape.

In some embodiment, each of the cross-sections discussed above regarding opening 104, first side (or surface) 106, second side 108, opening 110, first lip 120, second lip 124, and pleat 140 may be taken in generally parallel planes, which may be easily identified in FIG. 2 as the plane defined by, first side (or surface) 106 of base portion 90 of face mask 16.

As discussed above, in some embodiments, second lip 124 of bellows 24 may be removably secured to or adjacent opening 110 formed in tube 34 by a bellows clip 130. In some embodiments, bellows clip 130 may be substantially rigid. Bellows clip 130 may include a pair of arms 144 configured to clip onto, or around, sides of mask body 12. Mask body 12 may include one or more clip guides 146 configured to receive and/or guide arms 144 in order to secure bellows clip 130 to mask body 12. In some embodiments, bellows clip 130 may be removed by supplying sufficient force to pull clip 130 away from mask body 12.

Gas delivery conduits 14 may include any one or more gas delivery conduits for delivering gas from a gas source (e.g., a tank, ventilator, or wall line) to the subject via face mask 16. Gas delivery conduits 14 may also include one or more conduits or pathways for carrying exhaled gas away from the subject. As discussed above, in the particular embodiment shown in FIGS. 1 and 2, gas delivery conduits 14 may include at least conduit 14a and tube portion 34 of mask body 12.

Gas delivery conduits 14 may have any suitably configuration and may be formed from any suitable material for conducting gas along a gas delivery pathway. In some embodiments, one or more gas delivery conduits 14 may be flexible. For example, one or more gas delivery conduits 14 may comprise flexible tubes or hoses formed from any suitably flexible material, e.g., any suitably plastic, polymer, rubber or silicone. In the embodiment shown in FIGS. 1 and 2, gas delivery conduit 14a may comprise a substantially flexible (e.g., flexible plastic) tubing and tube portion 34 may comprise a substantially rigid (e.g., hard plastic) tubing.

FIG. 3 illustrates a partially exploded view of face mask 16, bellows 24 and bellows clip 130, according to one embodiment of the disclosure. In particular, FIG. 3 illustrates cushion portion 92 of face mask 16, bellows 24 coupled (e.g., removably coupled) to base portion 90 of face mask 16, and bellows clip 130. As discussed above, in some embodiments, cushion portion 92 may be substantially flexible and base portion 90 may be substantially rigid.

In this embodiment, cushion portion 92 may include a number of tabs 94 proximate an outer perimeter of cushion portion 92 and extending toward base portion 90. Such tabs 94 may be received and removably locked into place in slots 96 formed proximate an outer perimeter of base portion 90. In addition, bellows 24 may be coupled (e.g., removably coupled) to base portion 90 of face mask 16 in any suitable manner. For example, a first lip 120 (see, e.g., FIG. 2) may be removably secured to an inner edge 122 (see, e.g., FIG. 2) defined by opening 104 formed in base portion 90.

In this embodiment, each of base portion 90, cushion portion 92, first lip 120 of bellows 24, second lip 124 of bellows 24, pleat 140 of bellows 24, and opening 110 formed in bellows clip 130 may have a generally triangular (e.g., a rounded triangular) shape or cross-section. In other embodiments, one or more of base portion 90, cushion portion 92, first lip 120 of bellows 24, second lip 124 of bellows 24, pleat 140 of bellows 24, and opening 110 formed in bellows clip 130 may have any other suitable shape or cross-section.

FIG. 4 illustrates a side view of bellows 24, according to one embodiment of the disclosure. Bellows 24 may include a first lip 120, a second lip 124, and a single pleat, or fold, 140 located generally between first lip 120 and second lip 124. In other embodiments, bellows 24 may include multiple pleats or folds.

As discussed above with respect to FIG. 2, first lip 120 may have a cross-sectional area $A_{120}$, second lip 124 may have a cross-sectional area $A_{124}$, and pleat 140 may have a cross-sectional area $A_{140}$. In some embodiments, cross-sectional area $A_{140}$ of pleat 140 may be substantially larger than one or both cross-sectional areas $A_{120}$ and $A_{124}$ of first and second lips 120 and 124. In the particular embodiment shown in FIG. 3, cross-sectional areas $A_{120}$ of first lip 120 is larger than cross-sectional areas $A_{124}$ of second lip 124 and cross-sectional area $A_{140}$ of pleat 140 is substantially larger than each of cross-sectional areas $A_{120}$ and $A_{124}$.

The configuration, shape, and/or dimensions of bellows 24, and/or the materials from which bellows 24 is formed, may be selected to provide a particular or desired flexibility, rigidity, and/or resiliency of bellows 24 in any particular direction. For example, in some embodiments, bellows 24 is configured such that bellows 24 provides relatively little resilience or resistance preventing or resisting the movement of either side 100 or 108 of bellows 24 toward the opposite side, e.g., as indicated by arrow 148. In a particular embodiment, bellows 24 is configured such that bellows 24 provides substantially no resilience or resistance preventing or resisting the movement of either side 100 or 108 of bellows 24 toward the opposite side, e.g., as indicated by arrow 148.

In some embodiments, bellows 24 may be formed from a material, e.g., a plastic, polymer, or silicone, having a durometer hardness of less than 50 shore A. In particular embodiments, bellows 24 may be formed from a material having a durometer hardness of approximately 40 shore A. For example, in one embodiment, bellows 24 may be formed from a silicone having a durometer hardness of approximately 40±5 shore A.

FIG. 5 illustrates an exploded view of mask body 12 and exhaust port 50, according to one embodiment of the disclosure. In this embodiment, mask body 12 includes a first section 12a and a second section 12b that may be permanently or removably coupled to each other in any suitable manner, such as by adhesive or molding, for example. Constructing mask body 12 from multiple parts, e.g., sections 12a and 12b shown in FIG. 5, may increase the ease of manufacturing mask body 12. For example, separate parts of mask body 12 may be molded separately and then joined in any suitable manner.

FIG. 6 illustrates an example embodiment of a mask apparatus 10 secured to a subject's head 150, according to one embodiment of the disclosure. In this embodiment, an upper strap portion 80 may be secured to upper strap supports 60b associated with strap guide 62, which may be coupled to tube portion 34, thus securing tube portion 34 adjacent the subject's forehead. Upper strap portion 80 may extend around the subject's head at a location above the subject's ears. Strap guide 62 may be slided to a desired position along a length of tube portion 34 such that tube portion 34 is desirably oriented relative to the subject's head and/or such that face mask 16 is desirably oriented relative to the subject's face (e.g., to reduce or minimize the leaking of gas between face mask 16 and the subject's fact). In addition, cushion portion 78 of strap guide 62 may interface with the subject's head (e.g., the forehead), which may provide increased comfort for the subject.

In addition, a lower strap portion 82 may be secured to lower strap supports 60a coupled to a lower portion of mask body 12, thus securing the lower portion of mask body 12 adjacent the subject's nose and/or mouth. Lower strap portion 82 may extend around the subject's head at a location below or across the subject's ears.

Securing lower strap portion 82 and/or upper strap portion 80 to the subject's head may secure face mask 16 against the subject's face, e.g., against the subject's nose and/or mouth, such that gas may delivered to and/or removed from the subject's nose and/or mouth. As discussed above, bellows 24 may flexibly couple face mask 16 to tube portion 34 such that face mask 16 may move (e.g., rotate and/or translate) in various directions relative to tube portion 34. Such flexibility and/or adjustability of the orientation of face mask 16 relative to tube portion 34 may provide, e.g., increased comfort to the subject and/or reduced leakage of gas between face mask 16 and the subject's face.

As discussed above, tube portion 34 may be curved such that tube portion 34 extends upward adjacent the subject's forehead and/or curves over the forehead and extends at least partially toward the back of the user's head.

FIGS. 7A and 7B illustrate the adjustability of mask apparatus 10 for use with different sized heads, according to one embodiment of the disclosure. More particularly, FIG. 7A is a side view illustrating mask apparatus 10 secured to a relatively large head 150a, such as an adult's head, for example, and FIG. 7B is a side view illustrating mask apparatus 10 secured to a relatively small head 150b, such as a child or infant's head, for example. Head strap(s) 20 are not shown in FIG. 7A or 7B for the sake of clarity.

Each of FIGS. 7A and 7B illustrates a tube portion 34, a strap guide 62 supporting tube portion 34 proximate the relevant head 150a/150b, a face mask 16 interfacing the relevant face, a bellows 24 flexibly coupling face mask 16 to tube portion 34, and a bellows clip 130 securing face mask 16 to tube portion 34.

As discussed above, strap guide 62 may be slided to a desired position along a length of tube portion 34 such that tube portion 34 is desirably oriented relative to the subject's head 150a/150b and/or such that face mask 16 is desirably oriented relative to the subject's face (e.g., to reduce or minimize the leaking of gas between face mask 16 and the subject's fact). Bellows 24 may allow face mask 14 to flex relative to tube portion 34, which may allow face mask 14 to be properly oriented relative to the subject's face regardless of the orientation of tube portion 34 relative to face mask 16, at least within a particular range. For example, as shown in FIG. 7A, to fit a first sized head 150a, tube member 34 may flex in a first direction relative to face mask 16, which may extend an upper portion 160 of bellows 24. In contrast, to fit a second sized head 150b, tube member 34 may flex in a second direction relative to face mask 16, which may extend a lower portion 162 of bellows 24. Thus, in certain embodiments, due at least to (a) the adjustability of strap guide 62 relative to tube portion 34 and/or mask body 12 and/or (b) the flexible coupling between face mask 16 and tube portion and/or mask body 12 provided by bellows 24, mask assembly 10 may be suitably or desirably secured to various sized/shaped heads and/or faces.

Figure 8A:
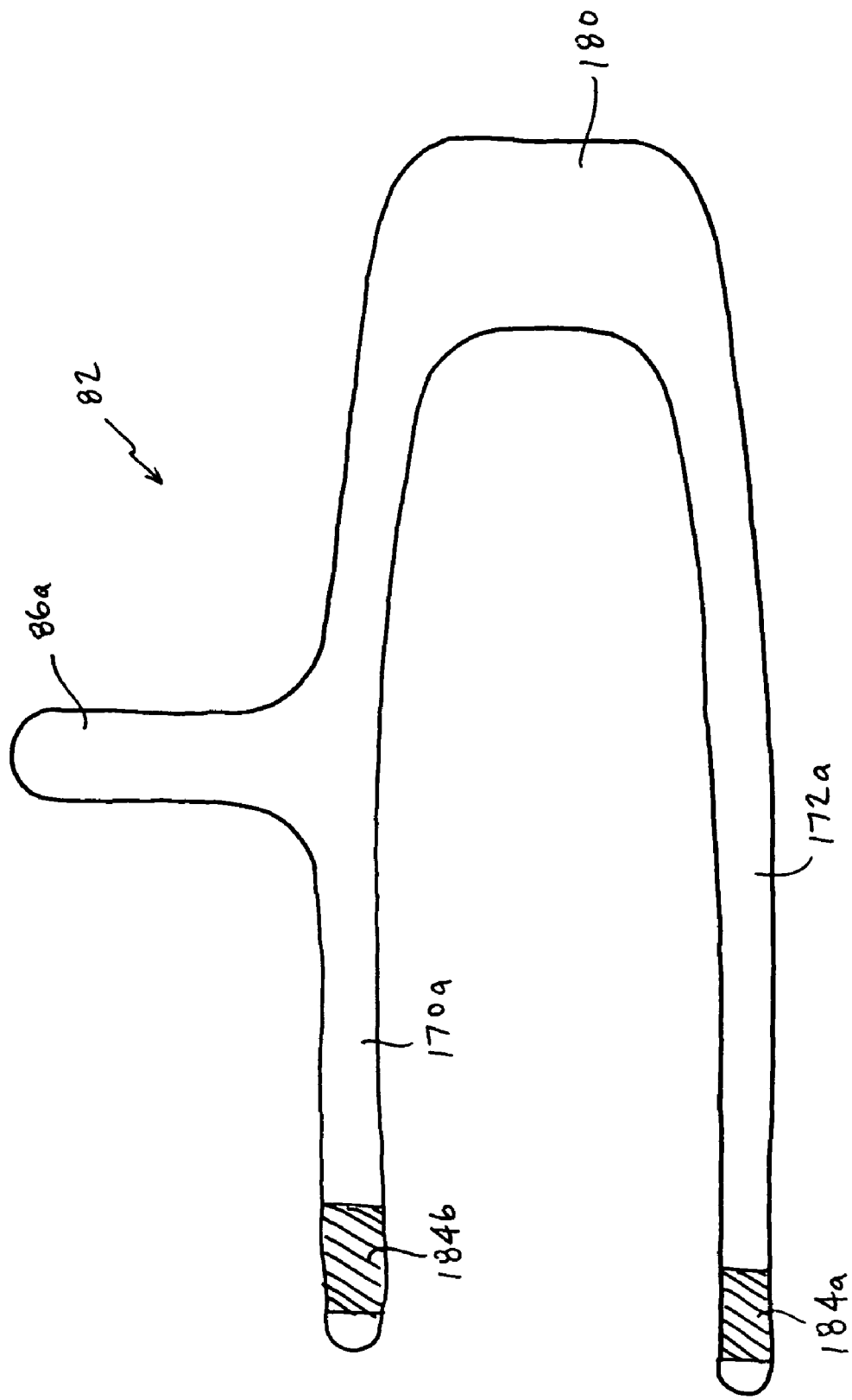
FIGS. 8A and 8B illustrate separate strap portions of a head strap that may cooperate to secure a mask assembly to a subject's head, according to one embodiment of the disclosure.
Figure 8B:
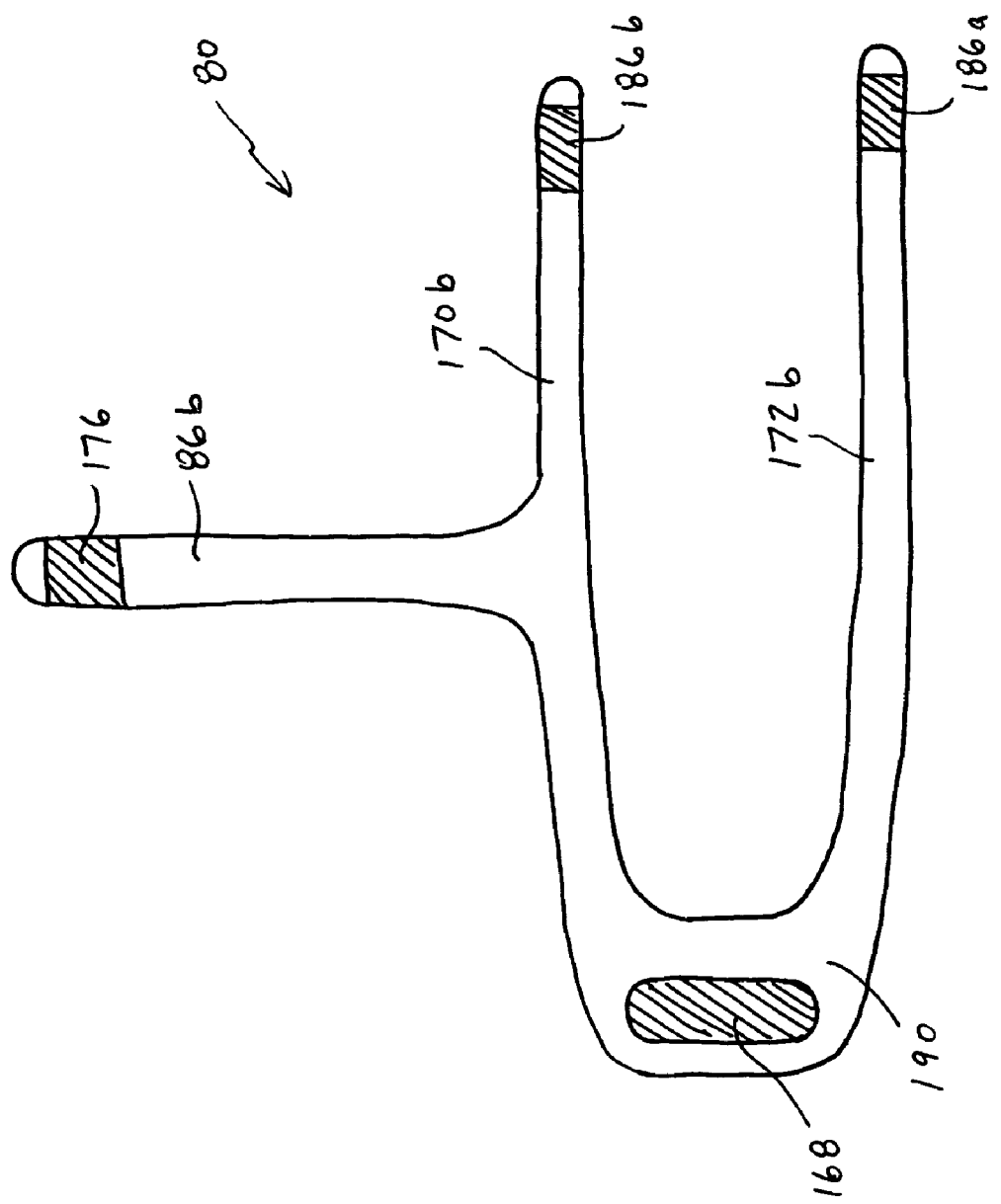

FIGS. 8A and 8B illustrate separate strap portions 80 and 82 of a head strap 20 that may cooperate to secure a mask assembly 10 to a subject's head, according to one embodiment of the disclosure. As shown in FIG. 8A, strap portion 82 may include an upper strap 170a and a lower strap 172a extending from a body portion 180. Upper strap 170a and/or lower strap 172a may include one or more hook and loop fastener (e.g. Velcro™) portions 184 configured for securing upper strap 170a and/or lower strap 172a to strap supports 60. For example, a hook and loop fastener portion 184a coupled to lower strap 172a may be configured to secure lower strap 172a to a strap support 60a, and a hook and loop fastener portion 184b coupled to upper strap 170a may be configured to secure upper strap 170a to a strap support 60b.

Body portion 180 may be configured to be secured (e.g., removably) to a body portion 190 of strap portion 80 (see FIG. 8B) to secure mask assembly 10 to the subject's head. Strap portion 82 may also include a support portion 86a configured to be secured (e.g., removably) to a support portion 86b of strap portion 80 (see FIG. 8B) in any suitable manner.

As shown in FIG. 8B, strap portion 80 may include an upper strap 170b and a lower strap 172b extending from a body portion 190. Upper strap 170b and/or lower strap 172b may include one or more hook and loop fastener (e.g. Velcro™) portions 186 configured for securing upper strap 170b and/or lower strap 172b to strap supports 60. For example, a hook and loop fastener portion 186a coupled to lower strap 172b may be configured to secure lower strap 172b to a strap support 60a, and a hook and loop fastener portion 186b coupled to upper strap 170b may be configured to secure upper strap 170b to a strap support 60b.

Body portion 100 may be configured to be secured (e.g., removably) to a body portion 180 of strap portion 82 (see FIG. 8A) to secure mask assembly 10 to the subject's head. Strap portion 80 may also include a support portion 86b configured to be secured (e.g., removably) to a support portion 86a of strap portion 82 (see FIG. 8A) in any suitable manner. For example, support portion 86b may include a hook and loop fastener (e.g. Velcro™) portion 176 configured for removably securing support portion 86b to support portion 86a.

It should be understood that hook and loop fastener portions 168, 176, 184 and/or 186 may be positioned at any suitable locations and/or on either or both sides of strap portion 80 and/or strap portion 82.

In certain embodiments, all or portions of strap portions 80 and/or 82 may be formed from a substantially flexible material, such as an elastic or a similar material. In other embodiments, head strap 20 may be formed from a less flexible material, such as neoprene, breathoprene, cloth, fabric, or other similar material.

FIGS. 9A-9D illustrate an example method of securing a mask assembly 10 to a subject's head by securing strap portions 80 and 82 of a head strap 20 to each other, according to one embodiment of the disclosure.

FIG. 9A illustrates a subject preparing to secure a mask assembly 10 to his head. The subject may grasp body portions 180 and 190 of strap portions 82 and 80. FIG. 9B illustrates the subject placing the mask assembly 10 against his head by pulling mask assembly 10 toward the face using body portions 180 and 190 of strap portions 82 and 80. FIG. 9C illustrates the subject securing mask assembly 10 to his head using strap 20. For example, the subject may secure body portion 180 of strap portion 82 to body portion 190 strap portion 80 in any suitable manner. In a particular embodiment, the subject may secure body portion 180 to body portion 190 using one or more hook and loop fastener portions, e.g., hook and loop fastener portion 168 shown in FIG. 8B. FIG. 9D illustrates the mask assembly 10 secured against the subject's head, e.g., after using the method shown in FIGS. 9A-9C.

It should be understood that in other embodiments, mask assembly 10 may be secured to a subject's head in any other suitable manner and/or using any other suitable straps or other securing devices.

Although the disclosed embodiments have been described in detail, it should be understood that various changes, substitutions and alterations can be made herein without departing from the spirit and scope of the disclosure as illustrated by the following claims. For example, it should be understood that in various embodiments, gas delivery mask apparatus 10 may include any combination of one, some or all of the various components and/or features discussed above and/or any one or more additional components and/or features.

What is claimed is:
1. A gas delivery mask apparatus, comprising:
 a mask body including a tube configured to extend upwardly adjacent a subject's forehead;
 a face mask configured to deliver gas to the subject, the face mask including a flexible cushion portion configured to interface with the subject's face and a substantially rigid base portion configured to support the cushion portion and including an inner edge; and
 a bellows including a lip configured for removably coupling the bellows to the inner edge of the substantially rigid portion of the face mask, the bellows being flexible to allow movement of the face mask relative to the tube.
2. A mask apparatus according to claim 1, wherein the bellows provides substantially no resiliency to resist movement of the face mask toward the tube.
3. A mask apparatus according to claim 1, wherein the bellows is formed from a material having a durometer hardness of less than 50 shore A.
4. A mask apparatus according to claim 1, wherein the bellows is formed from a material having a durometer hardness of approximately 40 shore A.
5. A mask apparatus according to claim 1, wherein the bellows includes a single pleat having a generally triangular perimeter.
6. A mask apparatus according to claim 1, further including a substantially rigid clip configured to removably secure the bellows to the tube.
7. A mask apparatus according to claim 1, wherein the bellows is separable from the face mask.
8. A mask apparatus according to claim 1, wherein the flexible portion of the face mask is separable from the substantially rigid portion of the face mask.

9. A mask apparatus according to claim 1, further comprising:
   a head strap configured to secure the mask body adjacent the subject's head; and
   a strap support configured to support the head strap, the strap support being movably coupled to the curved tube such that the strap support may be selectively positioned along a length of the curved tube according to one or more dimensions of the subject's head.

10. A gas delivery mask apparatus, comprising:
    a mask body including a curved tube configured to extend upwardly adjacent a subject's forehead;
    a face mask configured to interface with the subject's face to deliver gas to the subject, the face mask being flexibly coupled to the mask body such that the face mask may move relative to the mask body;
    a head strap configured to secure the mask body adjacent the subject's head; and
    a strap support configured to support the head strap, the strap support being movably coupled to the curved tube such that the strap support may be selectively positioned along a length of the curved tube.

11. A mask apparatus according to claim 10, wherein the curved tube is configured to extend generally over the subject's forehead and toward the back of the subject's head.

12. A mask apparatus according to claim 10, wherein the strap support is disposed around the curved tube such that the strap support is slidable along a length of the curved tube.

13. A mask apparatus according to claim 10, wherein:
    the face mask includes a flexible cushion portion configured to interface with the subject's face and a substantially rigid base portion configured to support the cushion portion; and
    the mask apparatus further comprises a bellows configured to couple the tube with the substantially rigid base portion of the face mask, the bellows being flexible to allow movement of the face mask relative to the tube.

14. A mask apparatus according to claim 13, wherein the bellows provides substantially no resiliency to resist movement of the face mask toward the tube.

15. A mask apparatus according to claim 13, wherein the bellows is formed from a material having a durometer hardness of less than 50 shore A.

16. A mask apparatus according to claim 13, wherein the bellows is formed from a material having a durometer hardness of approximately 40 shore A.

17. A mask apparatus according to claim 13, wherein the bellows includes a single pleat having a generally triangular perimeter.

18. A mask apparatus according to claim 13, further including a substantially rigid clip configured to removably secure the bellows to the tube.

19. A mask apparatus according to claim 13, wherein the bellows is separable from the face mask.

20. A gas delivery mask apparatus, comprising:
    a mask body including a tube configured to extend upwardly adjacent a subject's forehead;
    a face mask configured to deliver gas to the subject, the face mask including a flexible cushion portion configured to interface with the subject's face and a substantially rigid base portion configured to support the cushion portion; and
    a bellows configured to couple the tube with the substantially rigid base portion of the face mask, the bellows being flexible to allow movement of the face mask relative to the tube, wherein:
    the tube includes a first opening having a first cross-sectional area in a first plane;
    the substantially rigid base portion of the face mask includes a first surface having a second opening formed therein, the first surface having a second cross-sectional area in a second plane, the second opening having a third cross-sectional area in a third plane; and
    the bellows includes:
       a first portion configured to be coupled to the second opening;
       a pleat portion having a fourth cross-sectional area in a fourth plane; and
       a third portion configured to be coupled to the first opening;
    the first, second, third and fourth planes are substantially parallel to each other; and
    the second and fourth cross-sectional areas are greater than the third cross-sectional area.

21. A mask apparatus according to claim 20, wherein the third cross-sectional area is significantly greater than the first cross-sectional area.

22. A mask apparatus according to claim 20, wherein each of the first, second, third, and fourth cross-sectional areas have a substantially triangular shape.

23. A gas delivery mask apparatus, comprising:
    a mask body including a tube configured to extend upwardly adjacent a subject's forehead;
    a face mask configured to deliver gas to the subject, the face mask including a flexible cushion portion configured to interface with the subject's face and a substantially rigid base portion configured to support the cushion portion;
    a bellows configured to couple the tube with the substantially rigid base portion of the face mask, the bellows being flexible to allow movement of the face mask relative to the tube; and
    a bellows clip configured to couple the bellows to the mask body.

24. A gas delivery mask apparatus, comprising:
    a mask body including a tube configured to extend upwardly adjacent a subject's forehead and having a first opening in a first plane;
    a face mask including a cushion portion having a second opening in a second plane, and a base portion having a third opening in a third plane;
    a bellows configured to couple the tube with the face mask, and having a fourth opening in a fourth plane; and
    the first, second, third, and fourth planes are substantially parallel to each other.

* * * * *